United States Patent [19]
Winsel

[11] Patent Number: 5,242,565
[45] Date of Patent: Sep. 7, 1993

[54] DEVICE FOR ELECTROCHEMICAL GENERATION OF GASES FOR THE TRANSPORTATION OF FLUIDS AND SIMILAR MEDIUMS

[76] Inventor: August Winsel, D-Fasanenstr. 8 a, D-6233 Kelkheim, Fed. Rep. of Germany

[21] Appl. No.: 727,877

[22] Filed: Jul. 10, 1991

Related U.S. Application Data

[63] Continuation-in-part of Ser. No. 372,346, Jul. 10, 1989, abandoned.

[51] Int. Cl.[5] ............................................. C25B 9/00
[52] U.S. Cl. ................................... 204/265; 204/266; 204/291; 204/283
[58] Field of Search ............... 204/252, 283, 284, 253, 204/266, 258, 290 R, 292, 291, 264, 400; 429/44, 42, 27, 229, 54, 50, 90, 61, 66, 150, 224, 206, 186, 18, 190, 209

[56] References Cited

U.S. PATENT DOCUMENTS

| | | | |
|---|---|---|---|
| 3,622,397 | 11/1971 | Belove | 429/55 |
| 4,189,526 | 2/1980 | Cretzmeyer et al. | 429/13 |
| 4,402,817 | 9/1983 | Maget | 204/301 |
| 4,489,141 | 12/1984 | Stafford et al. | 429/61 |
| 4,556,612 | 12/1985 | Thibault et al. | 429/54 |
| 4,800,139 | 1/1989 | Kenjyo | 429/42 |
| 5,043,234 | 8/1991 | Tomantschger et al. | 429/229 |

*Primary Examiner*—John Niebling
*Assistant Examiner*—Kathryn Gorgos
*Attorney, Agent, or Firm*—Rosen, Dainow and Jacobs

[57] ABSTRACT

The device according to the present invention comprises a galvanic cell including a gas generating electrode, a counter electrode and an aqueous electrolyte enclosed in a housing. The device has one or more openings, by which the generated gas is released to the environment. The device also contains means for electrically connecting said gas generating electrode and said counter electrode and for establishing a current flow between said gas generating electrode and said counter electrode for generating a predetermined quantity of gas by said gas generating electrode for release from said opening of said galvanic cell. The objective of the cell is to generate and release oxygen or hydrogen gas, thereby defining a new type of cell. The device is referred to as a "gas generator cell."

28 Claims, 6 Drawing Sheets

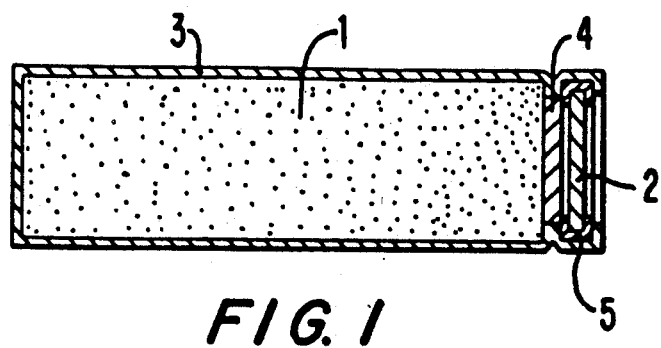
FIG. 1
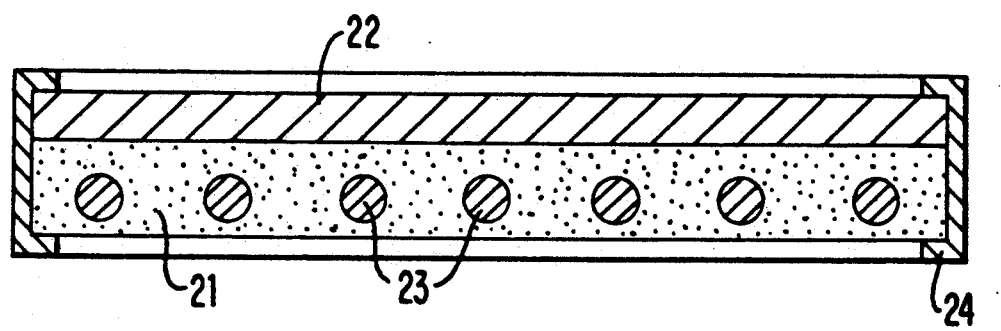
FIG. 2
FIG. 3
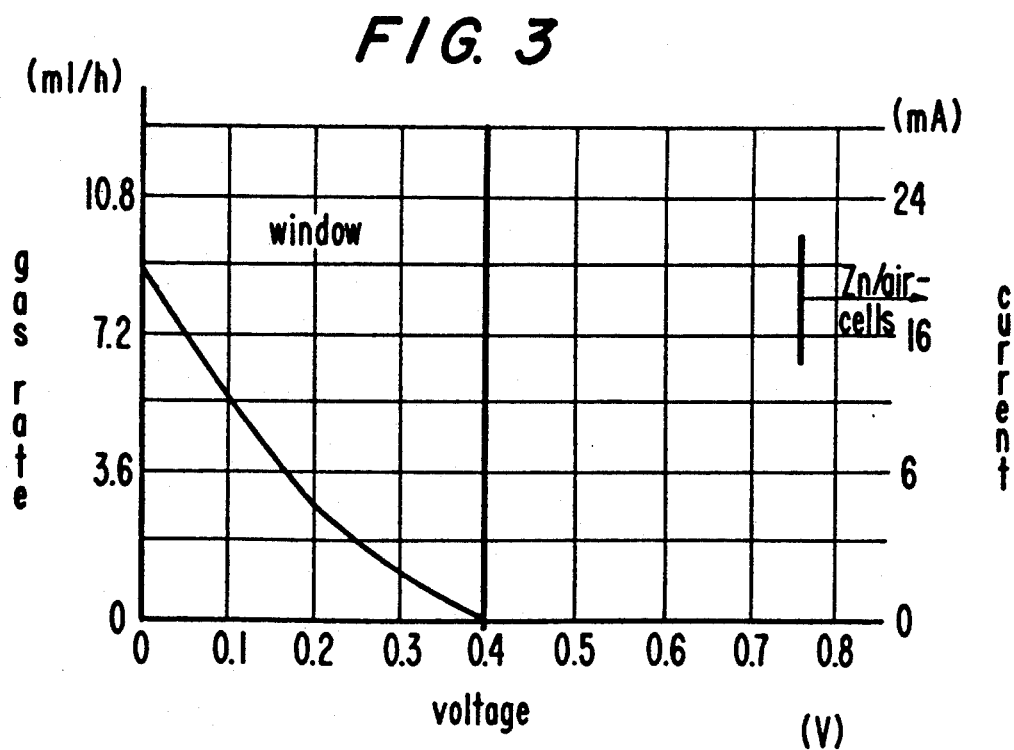

DEVICE FOR ELECTROCHEMICAL GENERATION OF GASES FOR THE TRANSPORTATION OF FLUIDS AND SIMILAR MEDIUMS

This application is a continuation-in-part of U.S. patent application Ser. No. 07/372,346 filed Jul. 10, 1990 now abandoned.

The present invention relates to a device for the electrochemical generation of gases for the transportation of fluids, lubricants and similar media.

DESCRIPTION OF THE PRIOR ART

It is known to use catalytic or electrochemical processes in order to generate gases as means for the transportation of fluids in technical applications. By catalytic decomposition of hydrazine into a mixture mainly consisting of hydrogen and nitrogen, a pressurized gas is generated, which is used to empty the water-filled tanks of submarines within a short time. The gas mixture contains ammonia in a concentration which is a function of the nature of the catalyst. The higher the concentration of ammonia, the higher is the temperature of the generated gas. This effect is used to operate the steering nozzles of satellites.

It is possible to use oxygen for similar purposes. The oxygen gas is generated by the catalytic decomposition of hydrogen peroxide using, for example, a silver catalyst. In both the hydrazine and hydrogen peroxide processes noted above, a high quantity of heat is liberated by the catalytic reaction, which in general requires a special heat management. The rate of the reaction is controlled by the influx of the liquid to the catalyst bed. Accordingly, in such a process, the reaction can only be regulated or stopped by regulating or interrupting the liquid flow. It has been proposed to use self-controlling catalytic reactors working similar to those used in the techniques of gas diffusion electrodes. Valve electrodes are disclosed in U.S. Pat. No. 3,201,282 and German patent 1,542,565. In these systems, the pressure of the generated gas is the control parameter; that is, by using a diluted aqueous solution of hydrazine (or hydrogen peroxide) the rate of the gas produced is kept constant, provided the discharged water effluent from the catalytic reactor is maintained constant.

It is possible to generate hydrogen by the corrosion of a base metal with an aqueous solution of an acid or a lye. For example, if zinc is brought into contact with hydrochloric acid, hydrogen is evolved and zinc is converted to zinc chloride.

In an alkaline solution, corrosion of zinc also leads to the formation of hydrogen. However, when using very pure zinc metal, no formation of hydrogen is observed because the zinc metal is passivated by the formation of a layer of zinc hydroxide on its surface, thus preventing the formation of hydrogen molecules. Both, zinc and zinc hydroxide, exhibit a high hydrogen overvoltage, which in turn stabilizes the existence of the metal in contact with water. If the zinc metal is contaminated by a metal such as iron, which exhibits a small hydrogen overvoltage, the corrosion and the evolution of hydrogen can be avoided by amalgamation of the zinc metal. This treatment has heretofore been used by the battery industry in order to avoid the hydrogen evolution in galvanic cells containing zinc as the anode metal. It is possible to accelerate the dissolution of a pure zinc sheet by contacting it with a platinum wire. Hydrogen evolution and corrosion of the zinc take place close to the area where the platinum contacts the zinc.

On the basis of the platinum wire/zinc experiment, a device for the generation of hydrogen was designed some years ago, which consists of a coin-like zinc plate with a center opening. Into this opening a bar of molybdenum is secured by any suitable means such as soldering. In order to generate hydrogen gas, this corrosion element (zinc/molybdenum) is submerged into a aqueous solution of KOH.

It is noted that in German patent 2 139 771 and Canadian patent 961,420, an automatic press for lubricants is described, which makes use of the above-mentioned metallic corrosion element. The hydrogen, which is generated by the corrosion element, drives a piston in a cylinder and forces the lubricant to penetrate from inside of the cylinder via a screw adapter to the lubrication object. The rate of this process depends on the properties of the corrosion element and on the temperature. Once the process has been started, no possibility exists to change the rate.

For many years zinc/air cells utilizing alkaline as well as acidic electrolytes have been on the market in different sizes. These cells consume oxygen gas to effect depolarization by extracting it from the air. These cells have not been used generally to produce a gas hitherto.

"An air depolarized cell", for example a "zinc/air cell", in operation is not able to produce a gas since its reaction is dependent on the presence of oxygen gas as part of the atmosphere in the cathode.

In various types of primary batteries, the development of gas has to be inhibited even in the discharged state or under abusive conditions in order to prevent damage of the apparatus driven by the cell. As noted, gas development in a primary cell caused by zinc corrosion or under abusive conditions leads to the development of high inside pressures and to the destruction of the cell and the apparatus. Therefore, it is an important goal of the research on primary cells to avoid the gas evolution by corrosion for example of the zinc or of iron containing construction elements.

In a typical zinc/air cell, as the result of corrosion of the zinc, hydrogen gas can develop at the zinc electrode which builds up a high pressure inside the cell and destroys it. This corrosion process takes place if impure, unamalgamated zinc has been used for the construction of the cell; it is not affected by the current taken from the cell.

It is unusual to speak about a "zinc/air cell" in connection with a gas evolving cell, since zinc/air cells exist in reality only if air as a part of the reaction is present in the cell.

Contrary to this, a hydrogen evolving cell in accordance with the present invention can only operate if oxygen is excluded from the cathode of the cell. Therefore, "gas evolving cell" defines a new category of cells which is not a part of the category of prior art "gas consuming cells", is not a part of the group of "air depolarized cells" or of "zinc/air cells" but which is antithetical to all of these. In a special, but important case, the "hydrogen evolving cell" and the "zinc/air cell" have in common the construction and the configuration of the electrodes. Certain types of zinc/air cells may be used as "hydrogen evolving cells" if oxygen is excluded from the cathode and an electric current is enabled to flow through the cell. This constitutes an important part of the present invention.

By definition, "anode" is that electrode or pole of a galvanic cell to which, by the action of an electric field, the negative "anions" are moved. "Cathode" is the second electrode of the cell, to which the positive "cations" are transferred. Therefore, "anode" and "cathode" only exist, if both electrodes of the cell are connected by an electronic conductor in order to form a closed circuit, and if, by the action of an internal and/or external voltage, a current is forced to flow through the cell. Anode and cathode are descriptions of the function of the electrodes in a working galvanic cell. For example, in a lead acid accumulator, the negative electrode is the anode of the cell during discharge of the accumulator, but it is the cathode during the recharge. Therefore, the terms "anode" and "cathode" define the cell and its electrodes in a respective function and, thus, are functional terms depending upon the behavior of the elements.

Within the hydrogen evolving cell of the present invention, the zinc electrode functions as the anode because the OH-anions move to this electrode where they are discharged. The hydrogen evolving electrode functions as the cathode because the positive H+ cations move to this electrode in order to be discharged there.

An optionally designed hydrogen evolving cell contains a hydrogen evolving electrode (cathode), which exhibits a hydrogen overvoltage as small as possible. For this reason, the hydrogen evolving electrode favorably contains metals like platinum, palladium or nickel for example. An optimally designed hydrogen evolving electrode should also have a reduction capacity as small as possible by containing little or no amounts of reducible metal oxides, because the reduction of such oxides reduces the amount of hydrogen which can be delivered by the cell. Further, an optimally designed hydrogen evolving cell contains a maximum volume of liquid and solid components at the beginning of the discharge, because the volume of these components is reduced by the hydrogen evolving reaction.

These demands for a standard hydrogen evolving cell and its proper design are contrary to those for a zinc/air cell. During discharge, the volume of the liquid and solid state components of the zinc/air cell are increased by the assimilation of the oxygen. Therefore, a reservoir or space area is required within the cell housing in order to accept the growing volume during discharge.

U.S. Pat. Nos. 4,105,830 to Kordesch and 4,189,526 to Cretzmeyer both describe "air depolarized" oxygen consuming "zinc air cells" but do not describe cells for the "evolution" of gases. Due to the teaching of the present invention it would be hindsight from the description of these cells to conclude that these cells contrary to their disclosures may be used as "hydrogen evolving cells" by simultaneously excluding oxygen from their cathodes and forcing electric currents to flow through the cells.

U.S. Pat. No. 3,976,502 to Sekido describes a "nickel-zinc alkaline storage battery" with means to promote the reaction between oxide and hydrogen evolved at the end of the charging process, a problem which mainly occurs in sealed cells. No teaching for a cell capable of evolving gas, (neither hydrogen nor oxygen) can be inferred from this patent.

U.S. Pat. No. 4,800,139 to Kenjyo describes a hydrogen electrode for fuel cells made from Raney-Ni comprising additional chromium and polytetrafluoroethylene.

An object of the present invention is to provide a device for the generation of a single gas at a variable or adjustable rate wherein the rate is expressed in quantity of gas per unit of time, or with a predetermined rate profile.

This device is compact, easy to manufacture, easy and safe to operate, and it does not pollute the environment.

Another object of this invention is to provide modes of safe and preferred methods of operation of this device.

DESCRIPTION OF THE DRAWINGS

FIG. 1 depicts a cross sectional side view of an oxygen generator cell.

FIG. 2 depicts a cross sectional view of the structure of a gas generating electrode according to the present invention.

FIG. 3 is a graph that illustrates the current/voltage-characteristic of a small hydrogen generator cell.

SUMMARY OF THE INVENTION

Figure 4:
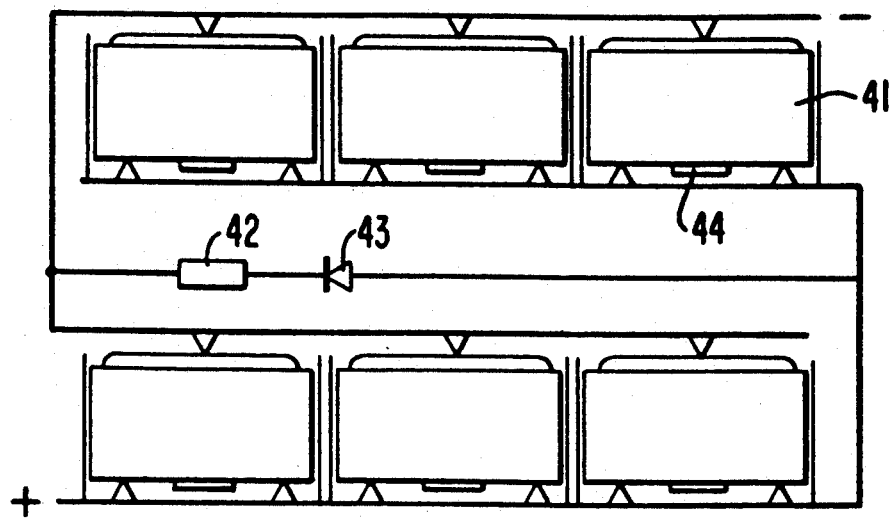
FIG. 4 depicts an arrangement of hydrogen generator cells.

The device according to the present invention comprises a galvanic cell including an anode, a cathode and an aqueous electrolyte enclosed in a housing (container). The container has one or more openings, by which the generated gas is released to the environment. This objective of the cell, is to generate and release a single gas, thereby defining a new type of cell. The cell of this category is referred to as a "gas generator cell".

The gas generator cell of the present invention is conveniently described using known electrochemical terms. It is well known that a voltage which is considerably larger than one calculates thermodynamically must be applied to an electrolyte cell to decompose water at measurable rates for the reaction $$H_2 + \tfrac{1}{2}O_2 \rightarrow H_2O \quad \Delta G_o = -56.96 \, kcal$$

$$E_0 = \Delta G_o/nF = 1.23 \, volts$$

The excess voltage over and above this decomposition voltage is usually designated with $\eta$ (eta) and is referred to as "overvoltage."

The overvoltage can be split into the part originating at the hydrogen evolving electrode and the part associated with the oxygen evolving electrode. Hydrogen overvoltage, then, is defined as the difference in potential between a hydrogen electrode at equilibrium and a hydrogen electrode subjected to cathodic current flow in the same electrolyte.

Similarly, oxygen overvoltage is defined as the difference in potential between an oxygen electrode at equilibrium and one being anodized with an external current. Thus, the expression "overpotential" is sometimes used instead of "overvoltage" for individual electrodes.

Overvoltage and current density are directly related. The dependence is described by the equation $$n = a + b \log i$$

where i is the current density, and a and b are constants. The fact that current and voltage of an electrode are mutually dependent on each other is observed not only for hydrogen and oxygen evolving electrodes but, in fact, for any electrode process, for example, metal dissolution, metal deposition, and electrochemical reduction or oxidation of dissolved species on redox electrodes. The general phenomena of a nonlinear current and voltage relationship is usually called "polarization." The terms "over-voltage" and "polarization" are, therefore, largely synonymous and often used interchangeably. However, overvoltage always refers to a deviation from the reversible potential of the particular reaction in question and is used with respect to the relation between current and voltage for one single reaction only. Polarization refers more generally to a change in potential, not necessarily from the reversible value, and not necessarily restricted to the effect of one single electrode reaction only.

There is a relation between overvoltage and catalytic activity of the metals to recombine hydrogen atoms. Both electrolytic hydrogen evolution and catalytic recombination, depend on the energy of adsorption of hydrogen atoms. It has been demonstrated that the hydrogen overvoltage, in general, decreases with increasing heat of adsorption. The adsorption energy in turn can be related to the cohesion energy, or sublimation energy, of the metals, and these, in turn, to electron concentration, surface energy, interatomic distance, compressibility, melting point, and electronic work function.

Electrochemical interfaces contain species other than protons and discharged hydrogen atoms. In particular, certain metals show very strong affinity to water or oxygen, in fact, so strong that these metals cannot be plated out from aqueous solution. The discharge of hydrogen on such metal surfaces as Mo, Ta, W, Zr, Nb, Cr, and Mn, proceeds with relative difficulty because of the strong affinity of oxygen to the surface. Cathode polarization may not remove the oxide films or adsorbed oxygen species completely. Hydrogen discharge then will take place on partially oxidized surfaces. The effect of the theoretically high adsorption energy of hydrogen on these metals is, thus, obscured by the strong affinity for oxygen. Hydrogen overvoltage thus depends on the relative adsorption energy of protons and foreign species.

Oxygen overvoltage is defined as the difference in potential between an oxygen electrode at equilibrium and one being oxidized with an external current.

The oxygen evolution process can be described by the overall equation $$2H_2O \rightarrow O_2 + 4H^+ + 4e^-$$

or $$4OH^- \rightarrow O_2 + 2H_2O + 4e^-$$

The reversible oxygen potential is extremely difficult, if not impossible, to realize experimentally, since oxygen evolution is always associated with the formation of surface oxides, or monomolecular chemisorbed oxygen layers, which tend to be electrochemically active by themselves. The oxygen evolution mechanism involving the formation of higher metal oxides (MeO) which subsequently decompose into lower oxides and oxygen according to $$MeO_n + H_2O \rightarrow MeO_{(n+1)} + 2H^+ + 2e^-$$

$$MeO_{(n+1)} \rightarrow MeO_2 + [(n-1)/2]O_2$$

has received much attention in the past. However, it is quite difficult to distinguish between higher oxides and chemisorbed oxygen species such as O, OH, $H_2O_2$, or $HO_2$.

The oxygen overvoltage follows accurately the equation, identical to the one for the evolution of hydrogen $$\eta = a + b \log i$$

whereby one observes for b the value $$b = +2.302RT/0.5F = 0.120 \text{ volts at } 25° C.$$

for a variety of different electrode materials.

The oxygen overvoltage usually is observed to increase slowly with time. It has been shown that this increase is linear with the logarithm of time. If the potential is held constant, the logarithm of the current correspondingly decreases linearly with the logarithm of time, over many hours. These slow changes of overvoltage must be connected with changes in the oxide film, such as slow chemisorption of oxygen species, increase in oxide film thickness, or by slow chemisorption of foreign anions.

The application of the gas generator cells in devices for transportation of fluids or similar media is described in connection with certain embodiments hereinafter and will in most cases, but not necessarily, proceed in a closed cell compartment, which under the influence of the generated gas volume changes its outer shape by movement of a piston or a membrane. Instead of this, the surface of the medium itself may form the membrane to result in the closed cell compartment. The shape change of the compartment causes the desired flow of the medium outside. In both cases, the generated gas remains in the cell compartment, which at the beginning is preferably as small as possible, especially if the gas generator cell generates hydrogen. At the beginning of operation the residual oxygen of the air is consumed easily by the hydrogen generator cell and therefore no explosive gas mixture is attained in this compartment. But, just prior to or after the fluid has been driven out of the device, the transport can be terminated by opening the cell compartment to the environment and releasing the compressed gas. For this purpose a valve or an adhesive backed label on an opening in the container wall can be provided. It can be opened by the action of the moving piston, which stresses a connection between the valve and the piston, FIG. 10.

A gas consuming electrode, which comprises a gas impermeable, electrolyte permeable layer contacting the electrolyte and adjacent the counter electrode and a gas permeable, electrolyte impermeable layer facing the gas converts the gas molecules into ions at the interface of both layers, from where these ions migrate into the electrolyte space of the cell. If the current is reversed, gas evolution will occur at the interface between electrolyte and electrolyte permeable layer, thus building up a high inside pressure until the electrolyte permeable electrode layer breaks through.

It is a feature of the present invention that the working layer of the gas evolving electrode consists of two intersecting cohering pore systems, one of which is filled with the electrolyte, the other with the gas by capillary action. This working layer is laminated with a porous hydrophobic PTFE layer. This construction establishes the lung-like electrochemical transpiration of a gas out of the cell.

The reverse process of the electrochemical oxygen consumption is the electrochemical oxygen evolution. In order to optimize the respective evolving reaction, the electrode must be designed for the evolution (not the consumption) of the respective gas. The teaching of the proper design of the electrodes to be used in a gas evolving cell is part of the instant invention.

In an air depolarized cell, the volume and weight of the material inside the cell is increased during operation, because the reduced oxygen molecules of the air are assimilated by the cell. Contrary to this, the volume and weight of the active materials in the cell of the present invention are decreased by the action of the gas evolving process. The optimal design of a gas evolving cell is different from that of a gas consuming cell.

The reaction product of the hydrogen evolving zinc cell is zinc oxide. Since it is in contact with the hydrogen, the zinc oxide cannot be reduced to zinc. Therefore, the separator between the zinc anode and the hydrogen evolving cathode is not required to be gas impermeable. This is in stark contrast to all gas consuming cells. There is a clear difference between hydrogen evolving cells and oxygen evolving cells in this respect. If the gas evolving reaction does not need external energy, the reaction product cannot consume the evolved gas without an external energy source. In this case a separator may allow the direct contact of the gas to the counter electrode. If an additional energy source is required for the gas production from the cell, the gas may be reconsumed by the partly discharged counter electrode. In this case, a gas impermeable separator, e.g. an ion exchange membrane, is necessary.

DESCRIPTION OF THE PREFERRED EMBODIMENTS

The invention is exemplified in FIGS. 1–10.

FIG. 1 depicts a cross sectional side view of an oxygen generator cell, comprising a cell container 3 for the housing of the metal oxide electrode 1, a separator 4, and the oxygen generator electrode 2. Sealing means 5 prevents the electrolyte from leaking outside of the area where it is contained and avoids an unintended short-circuiting. The gas evolution is started by establishing a current to flow between the metal container 1 and oxygen generator electrode 2.

When cell container 3 is constructed from zinc, the active material 1 is a zinc gel electrode and if 2 is a hydrogen generator electrode, this type of cell can deliver large amounts of hydrogen gas.

FIG. 2 depicts a cross sectional side view of the structure of a gas generator electrode according to the invention. A biporous working layer 21 bears conductor net 23. This layer 21 is faced to the interior of the cell. Hydrophobic layer 2 is laminated onto the working layer 21. The metallic frame 24 forms the electronic contact with the conductor net 23 and permits the electronic short circuiting of the cell depicted in FIG. 1.

FIG. 3 graphically illustrates an example of the current/voltage-characteristic of a small hydrogen generator cell. The gas rate of the cell as the current is shown as a function of the cell voltage. The "Window" shows the working range of the zinc based hydrogen generator electrode, and "zinc/air-cell" shows the working range of the zinc/air-cell.

FIG. 4 depicts the simple arrangement for the conditioning of zinc based hydrogen generator cells 41. By the use of an adhesive backed label 44, the air is maintained outside of the cell. The rectifying-diode 43 works like a Zener-diode and stabilizes the voltage of all the cells on the value of its forward voltage. Resistor 42 is also depicted in the circuit.

Figure 5:
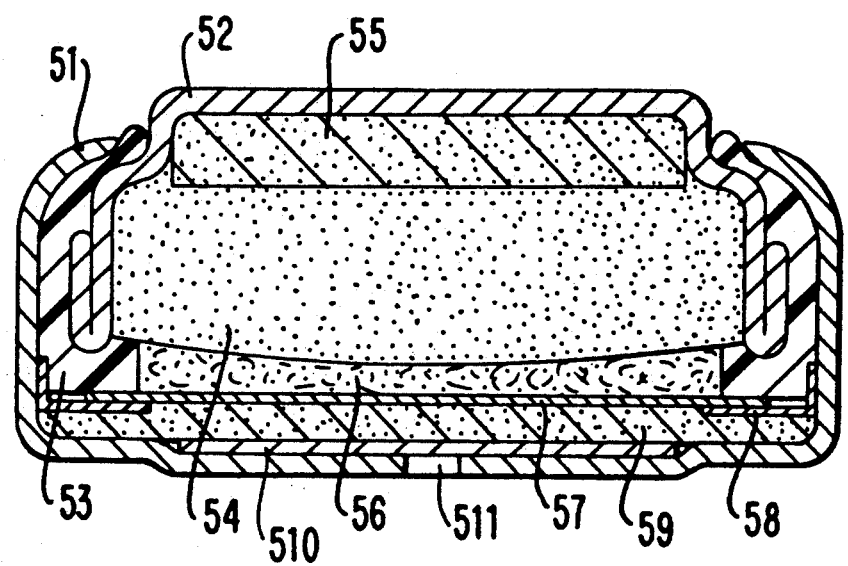
FIG. 5 depicts a cross sectional side view of a button cell constructed in accordance with the present invention.

FIG. 5 depicts a cross sectional side view of a button cell comprising a cup 51 and a cover 52 which together with a plastic seal 53 form the housing wall. Within the cover 52 and in contact with it, there is an active substance 54 in form of a zinc gel containing an electrolyte or in form of a porous tablet of a compound such as manganese dioxide. Compressible porous body 55 may contain an additional quantity of electrolyte. Element 56 is a fleece impregnated with electrolyte, and 57 is a separator in the form of an ion-exchange foil. This foil is kept in position by a support ring 58. An example of a gas diffusion electrode 59 is made of a Raney-nickel powder bound with PTFE and rolled into a net of nickel. On the side to the bottom of the cup 51 the gas diffusion electrode is provided with a foil of PTFE. Metallic support ring 58 is in contact with the gas diffusion electrode 59 and electrically connects the gas diffusion electrode 59 with cup 51. Element 510 is a wide-pore fleece layer which channels the gas generated in the gas diffusion electrode to opening 511 in the bottom of the cup from where it leaves the cell.

For example, in the instance where zinc is used, due to the fact that every zinc atom releases two electrons, one is thus able to reduce one molecule of water to hydrogen. Accordingly, it is necessary to react in the cell 18 grams of water for every 65 grams of zinc.

Figure 6:
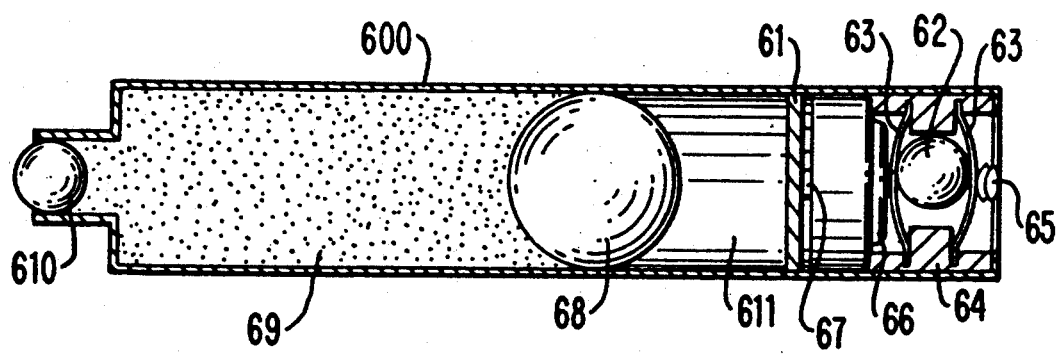
FIG. 6 depicts a cross sectional side view of a barostatically working roll-on-device.

FIG. 6 depicts a cross sectional side view of a barostatically working roll-on-device. Element 61 is a wall, which divides the cylindrical housing 600 of the device into two parts. On one (the right hand) side, there is the zinc based hydrogen generator cell with the positive pole 67 and the negative pole 66. Elements comprising 63 are two flexible metallized membranes with a ball 62 between them. The membranes are fastened in a holder 64. There is also provided an additional spring 65 which forces the membrane 63 to contact the minus pole 66 and thereby to shorten the circuit. The generation of gas builds up the pressure inside the device and moves membrane 63 to the right hand side of the contact 66. In area 611, ball 68 acts as a piston and presses medium 69, which can leave the piston via ball valve 610. This device compensates for the external pressure. In this embodiment, a pressure operated switch opens the circuit if a predetermined pressure is exceeded, and the switch closes when the pressure drops below predetermined value.

Figure 7:
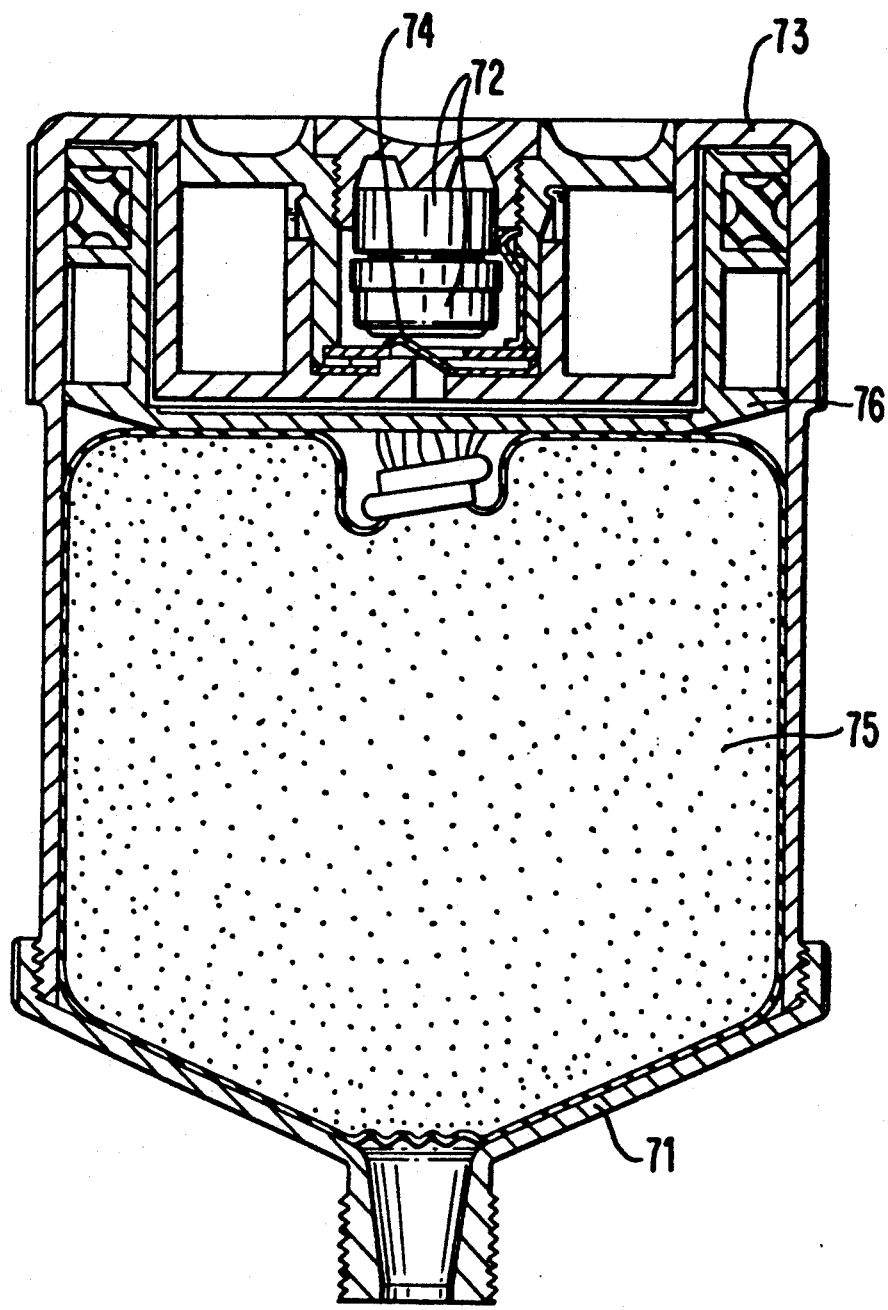
FIG. 7 depicts a cross sectional side view of a lubricant press containing hydrogen generator cells in series.

FIG. 7 depicts a cross sectional side view of a solid or fluid dispenser, more particularly a lubricant press 71 containing a solid or fluid exemplified by lubricant 75. It is operated by two hydrogen generator cells 72 in series connection. Both cells 72 are mounted in potentiometer ring 73, by which potentiometer 74 can be moved into the desired position. The resistance of the potentiometer determines the dispensing rate of the device, that is the result of movement of piston 76.

Figure 8:
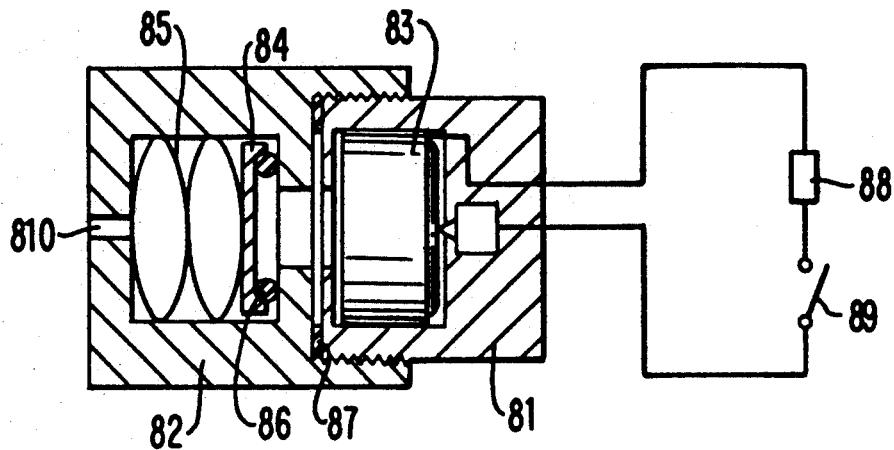
FIG. 8 depicts a cross sectional side view of a device that operates by means of the generating device of the present invention.

FIG. 8 depicts a cross sectional side view of a device for emitting hydrogen pulses from opening 810 each time the circuit between both poles of gas generator cell 83 has been closed by switch 89 via the outer resistance 88. The cell 83 is located in and threadedly joined to part 81 of the container 82 with gasket 87 between them. Two springs 85 close the cell compartment by pressing O-ring 86 hold in plate 84 against the housing. The spring force together with the o-ring area determines the opening pressure of the device.

Figure 9:
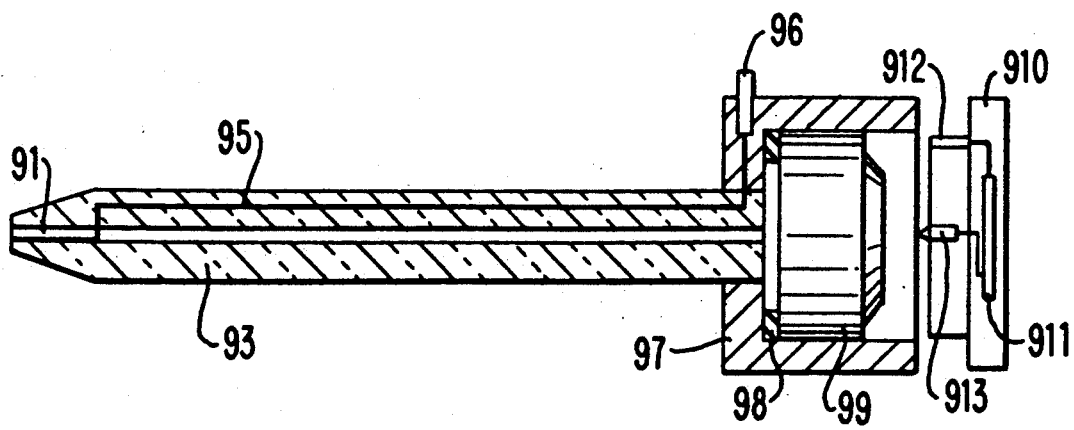
FIG. 9 depicts a cross sectional view of a hydrogen electrode device for electrochemical measurements.

FIG. 9 depicts a cross sectional side view of a hydrogen electrode device for electrochemical measurements having a platinized platinum wire 91 as a hydrogen electrode. This wire is inserted into the opening of a tube 93 preferably made of plexiglass or other similar material and is contacted by a wire 95 at contact screw 96. At the other end, the butt or tube bears cell container 97 with gasket 98 and hydrogen generator cell 99. The container is closed by cover 910, which bears contacts 912 and 913 and a potentiometer 911 in order to generate a sufficient amount of hydrogen for the hydrogen electrode. Such a hydrogen generator cell can feed the electrode 91 with hydrogen for a substantial period of time, for example, more than six months.

More particularly, the invention embodies two types of gas generator cells. The first type as illustrated in FIG. generates oxygen. It comprises a metal oxide counter electrode 1, preferably a metal oxide used in primary galvanic cells, e.g. manganese dioxide, silver oxide, mercury oxide, and an oxygen generating catalyst electrode 2. The oxygen generating catalyst electrode forms a part of the cell container 3, both together enveloping the metal oxide electrode 1, a separator 4 and an aqueous electrolyte solution, which preferably is an alkaline solution. In this "oxygen generator cell" the oxygen generator electrode consists of two layers, as is shown in FIG. 2.

The following layers are depicted in FIG. 2:

i) a working layer 21, comprising an electronically conducting double porous structure. This layer is exposed to and in contact with the separator, the electrolyte and the metal oxide electrode. The expression "double porous" specifies a structure which consists of two intersecting continuous pore systems, one of which is hydrophilic and saturated with or by the electrolyte, the second one is of hydrophobic nature and is filled with gas;

ii) a porous hydrophobic layer 22 adjacent to and in engagement with the working layer. This layer prevents the electrolyte from leaving the cell.

In order to generate oxygen, an electric current is forced to flow through the oxygen generator cell, which cathodically reduces the metal oxide electrode to the respective metal or to a minor oxidation state and which anodically develops oxygen at the oxygen generator electrode. Due to the unique structure of the oxygen generator electrode, the gas evolves at the three phase boundary formed in the hydrophilic pore system of the working layer, penetrates into the hydrophobic pore system of this layer and leaves the cell via the connected hydrophobic layer.

The present invention generally utilizes an electrocatalyst which for the purposes of this invention is a catalytic material that catalyzes reactions with electrons as one of the reaction partners. The electrocatalyst referred to is always an electrode because the other reaction partner is an ion. A typical electrocatalyst reaction is:

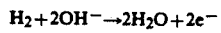

$$H_2 + 2OH^- \rightarrow 2H_2O + 2e^-$$

which is a reaction that only proceeds using some special metals such as Pt or metals that are presented in a special structural form such as Raney-Nickel.

Thus, in the present invention, it is advantageous to use an electrocatalyst in the biporous working layer 21 as shown in FIG. 2, which exhibits minimal overvoltage (or as small as possible) to the anodic oxygen evolution. Raney-Nickel powder is a preferred material to be used as the electrode in this instance. It is formed into the desired double porous structure by mixing it with a hydrophobic resin powder such as polytetrafluorethylene (PTFE) or polyethylene (PE). This kind of electrode has been described earlier by applicant in European patent specification EP 144,002 equivalent to the German patent application 3 342 969. Instead of Raney-Nickel, other powdered catalytic materials can be used for this purpose, as long as they are stable with respect to the electrolyte. The voltage of the cell depends on the type of metal oxide, on the type of electrocatalyst and on the current. However, the rate of the generated gas is equivalent to the current alone. In case of metal oxides with high oxidation potentials, like AgO and NiOOH, the cell voltage, as a function of the current, may change its sign (path through zero). For example, in the first voltage region, the cell reaction run in the standard manner that cell reactions normally proceed without an external energy source is necessary for further operation. Thus as noted, in order to realize a given rate at a given time, the current is stabilized by the aid of a direct current source, e.g. a primary battery, and an adjustable resistance.

Alternatively, instead of a metal oxide electrode, nitrate ions may work as a source of oxygen. In this case, a metal nitrate or ammonium nitrate as the active material is cathodically reduced at the counter electrode, i.e. the second electrode of the galvanic cell which transports the current in combination with the other electrode, while oxygen is evolved at the oxygen generator electrode.

Referring again to FIG. 1, in order to prevent the oxygen from flowing to the metal oxide electrode 1 and reoxidizing the reduced oxide, the separator 4 must form a barrier. Therefore, separator may be an ion exchange membrane or a porous hydrophilic membrane with a sufficient capillary pressure in order to avoid gas filled pores in separator 4. This may not be necessary, if the oxygen gas is non-reactive with the reduced species of the metal oxide electrode.

The second type of "gas generator cells" of the present invention as illustrated in FIG. 1 solely generates hydrogen. It provides a metal counter electrode 1, a "hydrogen generator electrode" 2 and an aqueous electrolyte, preferably an alkaline solution of KOH or NaOH in water. The metal electrode is preferably one of those, which are used in primary or secondary galvanic cells, such as zinc, cadmium and lead, but also copper can be used. The hydrogen generating catalyst electrode like its counterpart oxygen generating catalyst electrode described above forms a part of the cell container, both together enveloping the metal electrode 1, the separator 4, and the aqueous electrolyte solution contained therein.

In this "hydrogen generator cell" the "hydrogen, generator electrode" consists mainly of two layers. As shown in FIG. 2, these layers are:

i) a working layer 21 comprising an electronically conducting double porous structure; this layer is faced to the separator 4 of FIG. 1, to the electrolyte, and to the metal electrode 1 of FIG. 1. The term "double porous" or the term "biporous" again specifies a structure, which consists of two intersecting continuous pore systems, one of which is hydrophilic and saturated with the electrolyte, the second one of which is of hydrophobic nature and is filled with gas:

ii) a porous hydrophobic layer 22 is in close connection to biporous working layer 21. This layer 22 prevents the electrolyte from leaving the cell. In order to generate hydrogen, an electric current is forced to flow through the cell which anodically oxidizes the metal electrode to the respective metal oxide and which cathodically develops hydrogen at the hydrogen generator electrode. Due to the unique structure of the "hydrogen generator electrode", the gas evolves at the three phase boundary gas/electrolyte/catalyst, formed in the hydrophilic pore system of working layer 21. The gas then penetrates into the hydrophobic pore system of this layer and leaves the cell via the connected hydrophobic layer 22.

It is advantageous to use an electrocatalyst in working layer 21, which offers a small overvoltage to the cathodic hydrogen evolution. Raney-Nickel powder is a preferred material. It is formed into the desired double porous structure by mixing it with a hydrophobic resin powder such as polytetrafluoroethylene (PTFE) or polyethylene (PE) as described above and found in European patent specification EP 144,002. Instead of Raney-Nickel, other powdered catalytic materials can be used for this purpose, which are stable against and will not be oxidized nor reduced by the electrolyte. A very suitable material for this use is platinized or palladinized active carbon powder. Also, an active carbon/Raney-Nickel mixture can be used economically.

The voltage of the cell depends on the type of metal, on the type of electrocatalyst and on the current. However, the rate of the generated gas i.e. (amount of gas) generated per unit of time) is equivalent to the current alone.

Besides the use of Raney-Nickel, other Raney-metals of Group VIII of the periodic table of elements exhibit zero or very small hydrogen overvoltage. Therefore, the internal resistance in the circuit as a function of the current is nearly constant. In order to realize a given rate of gas generation for a given time period, the current can be stabilized by the aid of a direct current source, e.g. a primary battery, and an adjustable resistance.

In the course of this invention, zinc has proved to be the most suitable metal electrode for "hydrogen generator cells."Like in primary battery applications, it can be used in the form of a sheet zinc metal, as a pressed zinc powder electrode or as a so called "zinc gel electrode". A zinc sheet may form the cylindrically shaped cell housing as depicted in FIG. 1 containing within a zinc powder electrode or a zinc gel electrode and the other components of the cell. In its most simple application, the hydrogen generator cell with a zinc electrode does not need any external power source. In order to allow its proper operation, oxygen must be excluded from the pores of the "hydrogen generator electrode". Therefore, air is excluded from the cell by valves for example 84, 86 as shown in FIG. 8 or by adhesive label 44 on the openings, which are provided in the cell housing as depicted in FIG. 4 to release the generated gas. The voltage range of operation of the cell is between 0 V and 0.4 V as shown in FIG. 3. This voltage range is referred to herein as the "operation window." The open cell voltage of 0.4 V to 0.42 V depends generally on the composition and the concentration of the electrolyte. The current/voltage-characteristic relationship is substantially linear if a reversible working electrocatalyst like Pt, Pd or Raney-Nickel is used for the "hydrogen generator electrode"

A voltage of a zinc based hydrogen generator cell exceeding 0.5 V indicates a malfunction of the cell. But prior to the start of operation by short-circuiting, the cell voltage very often exceeds 0.5 V due the presence of oxides at the catalyst surface. These can be removed by conditioning the cell at 0.5 V to 0.7 V. A simple method can be realized by short-circuiting the cell via a rectifying diode in flux direction as shown in FIG. 4. This reduces all deleterious oxygen containing species on the gas generator electrode without evolving any hydrogen.

If a hydrogen generator cell with zinc as metal electrode is discharged in air or in a oxygen-rich environment, the voltage will remain above 0.8 V, but the cell will produce no hydrogen. In this instance, the cell works as a zinc/air cell as long as enough space is available inside the cell housing to retain the assimilated oxygen. If oxygen is excluded from a zinc/air cell of the common construction, and if this cell is short-circuited and if the cell voltage is allowed to fall below 0.4 V, this cell may evolve hydrogen, too. Thus, a gas consuming zinc/air cell is forced to operate as a "hydrogen generator cell". A zinc/air cell is a gas consuming cell; oxygen is an essential part of the cell and of its overall reaction. By contrast, "hydrogen generator cell" of the present invention produces hydrogen, which is a product but not an essential component of the cell. From these considerations it follows: Although the zinc-based hydrogen generator cell of the present invention and a common zinc-air cell appear similar in some details of construction, they show no equivalence because oxygen has to be excluded from the interior of the hydrogen generator cell, but is an essential part of the zinc/air cell. Zinc/air cell and the zinc based hydrogen generator cell operate with substantially different voltage windows.

An optimal designed hydrogen generator cell as shown in FIG. 1 and FIG. 5 contains a hydrogen generator electrode, which exhibits a hydrogen overvoltage as low as possible. For this reason, the hydrogen evolving electrode contains metals like platinum or palladium. Alternatively, nickel, which is favored due to its low price can also be used. In addition, an optimal designed hydrogen generator electrode should exhibit a reduction capacity as small as possible and, therefore, should contain only small amounts of reducible metal oxides because the reduction of such oxides reduces the amount of hydrogen, which can be delivered by the cell. An optimal designed hydrogen generator cell contains a maximum of water and zinc at the beginning of the discharge, zinc and water in such a ratio, as to give a maximum of hydrogen according to the equation $Zn + H_2O \rightarrow ZnO + H_2$.

The quantity of zinc and electrolyte, which have to be filled in into such housing, are depending on the quantity of hydrogen to be produced by the cell. For a production of 1 dm$^3$ of hydrogen, roughly 0.32 g Zn and 0.80 g H$_2$O are needed. The magnitude of the gas generator electrode only depends on the rate of gas evolution. For example, a rate of 0.04 Ndm$^3$/h of hydrogen corresponds to a current of 100 mA; for this current an electrode surface of 1 cm$^2$ is sufficient. In order to generate as much gas as possible using a gas generator cell of given internal space, the cell should contain as much reducible metal oxide as possible in case of an oxygen generator cell and, respectively as much oxidizable metal as possible in case of an hydrogen generator cell.

During discharge of the cell FIG. 5, the volume of the internal components is reduced by the release of the hydrogen gas. The same behavior of decreasing volume is true for the oxygen generator cell. To maintain contact between the solid and liquid phases involved in the respective reaction, the electrolyte may be pressurized, which can be done by introducing it with small over pressure into the wide pores of a hydrophobic body 55 or by using hydrophilic absorbent paper 56 in the important areas. It is also possible to maintain contact between zinc electrode 54, the respective conductor 52 and the separator 56 by means of a spring elements for example a sponge 55. The separator is hydrophilic and is arranged between the zinc electrode 54 and the gas generator electrode (that is between the counter electrode and the gas generator electrode).

Finally, it is possible to effect a change of volume from outside by deformation of the cell housing. These parameters for a hydrogen generator cell and its proper design are contrary to those for a zinc/air-cell. During discharge, the volume of the liquid and solid state components of the cell is increased by the assimilation of the oxygen. Therefore, during construction, empty space is left in the cell housing in order to absorb the growing volume during discharge.

It is a teaching of this invention, that a hydrogen evolving cell will function as a zinc/air-cell, if air is allowed to penetrate into the pores of the gas generator electrode. In this case, no hydrogen is released by the cell. The reason for this is the large reactivity of the oxygen, which reacts in contact with all electrochemical metals. It is also a teaching of this invention, that a "zinc-air cell" can release hydrogen, if air is excluded from the cell and the cell is operated below 0.4 V. Therefore, another embodiment of the present invention is in alteration of the intrinsic objective, certain types of so called zinc/air cells may be used as hydrogen evolving cells if oxygen is excluded from the cathode, and an electric current is enabled to flow through the cell at a voltage below 0.4 V. The current is enabled to flow by an electronic circuit, which shortens both electrodes of the cell. A zinc/air cell, from which air is excluded is in reality not a zinc/air cell since it does not contain an air cathode due to the lack of oxygen.

Some additional details of preferred applications of the present invention are described in FIG. 5 of the drawings. In FIG. 5, a zinc-based hydrogen generator cell is shown. The cell is designed as a button cell having cup 51, with a cover 52 of the cell housing gasket 53, zinc anode 54, electrolyte sponge 55, 56 is a fleece, porous separator or an unporous ion exchange membrane 57, hard ring 58, hydrogen generator electrode 59. Additionally, paper-like fleece 510 and opening 511 are provided to release the gas. If hydrogen diffuses back to the zinc electrode, no reaction can take place which can reduce the amount of the gas released by the cell.

In principle, an oxygen generator cell looks like the hydrogen generator cell depicted in FIG. 5. In this case, the cell contains reducible metal oxide electrode 54 and oxygen generator electrode 59. In some cases, the separator 56 of an oxygen generator cell has to prevent the generated oxygen from flowing back to the cathode 54, because the oxygen might be reconsumed by the reduced parts of the cathode material. In this embodiment, an ion exchange membrane would be optimal for the separator.

It is possible to operate the gas generator cell in a barostatic mode. This can be done by using a pressure operated switch to open the circuit when a predetermined pressure is attained. This is shown in FIG. 6.

For short intervals of time, it is possible to operate a hydrogen generator cell in a hydrogen consuming mode by increasing the voltage in the presence of hydrogen slightly above 0.4 V while reversing the current. Current reversal leads to an electrode position of zinc at the zinc electrode and to an electrochemical consumption of hydrogen. This reversal mode of operation can be used to reduce the pressure in the hydrogen driven device, if necessary. This might be of benefit, if a person, who is carrying a gas driven inject, is climbing on a tall mountain or is flying in a jet liner. But for this mode of reverse operation, an additional power source is required.

It is possible to use a number of gas generator cells in series connection. At the same current density, the voltage of the battery is n-times that of a single cell, and the generated rate of gas is n-times that of a single cell.

In order to operate a gas driven device at a constant rate, only a constant ohmic resistance is needed to short-circuit the zinc based hydrogen generator cell. But in order to quickly attain this state of operation, it is advantageous to start the generator cell by short-circuiting with a very small ohmic resistance and switch over to the final one later on.

If pulses of hydrogen are needed from time to time, it is useful to pulse the current by closing and opening an electric switch as shown in FIG. 8. The generated hydrogen quickly raises the pressure inside the cell, which is shunted against the device by an over pressure-valve. This valve opens after the electric switch has short-circuited the cell and the pressure has risen a predetermined value. When the switch opens, the pressure again falls under the closing pressure of the valve and so on.

The following examples show useful applications, which are based upon the new gas generator cells.

As shown in FIG. 7, a lubricant-press contains a piston 76 in a closed cylinder 71, which separates the lubricant-compartment 75 from the pressure-compartment. The gas generator cells 72 according to the invention are arranged within the compression compartment, e.g. in the endplate of this compartment. At the other end of the press, there is a mouth-piece to connect the press with the ball-bearing. If the gas generator cell is a zinc based hydrogen generator cell, the activation of the press can easily be done by short-circuiting the cell with a potentiometer 74, which of advantage is situated inside the pressure room but can be regulated by a screw or by potentiometer ring 73 from outside the press.

FIGS. 10(a) through (d) disclose various uses for the cell of the present invention. In an injection device for medical purposes, a piston or a membrane is dividing the cylindrical compartment in two parts, one of which contains the injection, the second one contains the gas generator cell and the expanding gas. In case of the zinc-based hydrogen generator cell, only one resistance in order to short-circuit the cell is needed for a nearly constant injection rate of the medicine. A button cell of about 10 mm in diameter and 5 mm in height is a sufficient for an injection of 20 ml within 10 h. In this application, the cell is mounted preferably on top of the injectee. By addition of a regulator circuit for the generator current, the injection rate can be adapted to a given profile.

Also, hydrogen electrodes are frequently used in order to measure the pH-value of aqueous solutions of salts, acids or bases. The hydrogen electrode consisting generally of a Pt-wire, which is encircled by hydrogen, is dipped into the solution which is to be measured for acidity or basicity. The problem is such an electrode is the need for a hydrogen source, which in general is contained in a heavy steel pressurized gas bottle. In FIG. 9, a device is shown, which consists of a hydrogen electrode at one end of a narrow pipe. At the other end, there is a hydrogen generator cell, which feeds the electrode with the hydrogen gas under the pressure needed for this purpose.

FIGS. 10 (a) through (d) show cross sectional views of a fluid dispensing device according to the invention with different means for terminating and eventually controlling the dispensing process. In applications of the present invention in the field of medicine, it is important that the continuous generation of gas by the gas generator cell 208 be stopped immediately at the end of the dispensing process. This is necessary to prevent an entry of the hydrogen gas into the human body due to an uncontrolled increase of the pressure. In FIGS. 10(a) through (d), cylinder 200 contains the piston 201, which is driven to the left hand side by the gas generated in cell container 208. As indicated in FIG. 10(b), container 208 contains the cell, the resistor, the switch 202 and other construction elements, which are necessary or of advantage to make use of the invention but need not to be shown in this particular case. The gas generated by the cell 208 is lead into cylinder 200, thereby driving the piston 201 to the left hand side and dispensing fluid 206 into the body. During this process, the plug 205 closes the valve. Piston 201 and plug 205 are connected by a line or thread 203 or a telescope 213 of a given length. When piston 201 reaches its destinated end position, thread 203 or telescope 213 are stretched. The force which has driven the piston 201 so far now acts on the plug 205 and opens the valve in FIG. 10(a), or it acts by telescope 213 on switch 202. Switch 202 is opened and the cell current in FIG. 10(b) is interrupted.

Figure 10A:
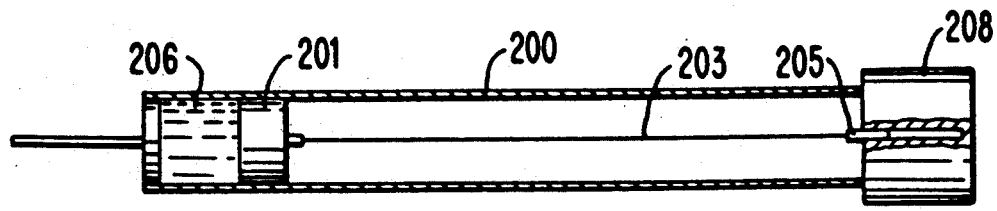
FIGS. 10(a)-(d) depict cross sectional view of embodiments of the present invention that can be used in various applications.
Figure 10B:
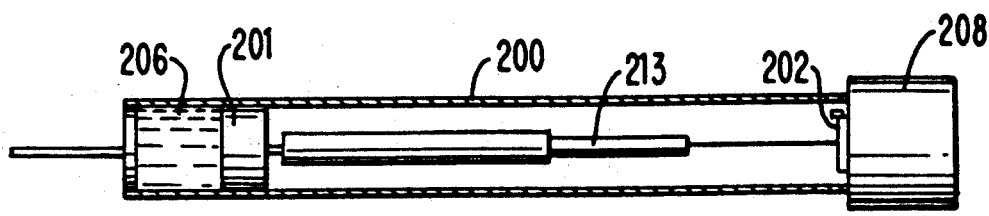

When valve 205 in FIG. 10(a) is opened the compressed gas in cylinder 200 is released to the environment and air enters cylinder 200. In case of the most frequently used zinc based hydrogen generator cell, the voltage of the cell indicates this as a "malfunction". The voltage sharply increases to more than 0.8 V and the hydrogen generation immediately stops. The result is merely the same as in the case of switching off the short-circuit in FIG. 10(b), but both methods can be combined, too.

Figure 10C:
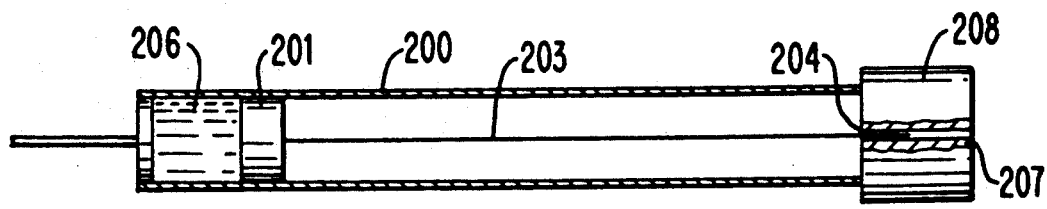

In a very simple construction as depicted in FIG. 10(c), the valve consists of a non porous thread 203 which is stressed by the action of the piston to move through a narrow hole 204 of a rubber-elastic plate 207.

So long as the piston has not arrived at its desired end position, the hole remains closed. But if the end of thread 203 has moved through the hole 204, the valve is open and the gas is released to the environment as described before.

Figure 10D:
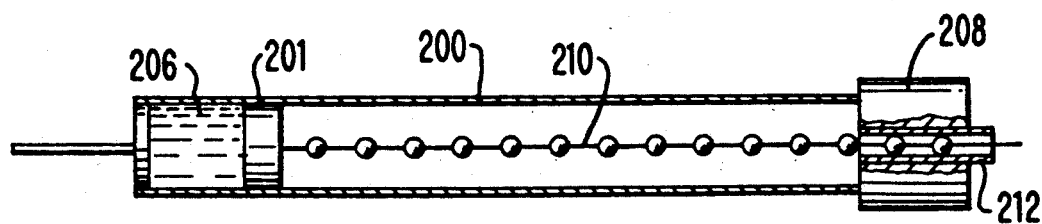

The construction depicted in FIG. 10(d) is called a "rosary valve" and comprises a chain of balls 210 of limited length. At one end it is fixed to the moving piston 201. This rosary chain 210 is towed through a narrow elastic pipe 212 long enough to have always two balls inside the pipe 212. If as a result of the movement of piston 201 the last ball has passed through pipe 212, this valve is open. The compressed gas can escape to the environment and air can enter cylinder 200.

The electrical circuit means depicted in FIGS. 10 (a) through (d) all act on the gas generator cell, either by interrupting the current or by promoting a malfunction. In case of FIG. 10(a) and (b), a force of the moving piston only acts in the very last moment of its movement. This is in contrast to FIGS. 10(c) and (d). In these embodiments, the force acts as long as the piston moves but falls to zero when the end of the thread 203 or the chain 210 has moved through the valve.

The diameter of thread 203 may be smaller after the desired length has moved through hole 204. In this case, the desired function of thread 203 in FIG. 10(c) is still guaranteed. The same is true for rosary chain 210, which may end in a ball-free thread with a finger slip-knot. Such an elongated thread has the advantage of pulling the piston in the reverse direction in order to recharge the device with the fluid 206.

These illustrative examples, provide evidence for useful applications of the gas generator electrode. These examples under appropriate modification can be converted to oxygen generator cells.

What I claim and desire to protect by Letters Patent is:

1. A device for electrochemically generating a hydrogen gas or an oxygen gas in an adjustable quantity, comprising:
    a galvanic cell including an enclosed housing having a base and at least one side wall integral with said base, a cover, a seal positioned between and in contact with said cover and said side wall of said housing, and an opening for releasing gas from said housing, said galvanic cell further including;
    a gas generating electrode forming a part of said housing and including an electron-conducting porous body contained within said housing;
    a counter electrode including an oxidizable metal or a reducible oxide or nitrate which serves in countercapacity to said gas generating electrode;
    separator means between said gas generating electrode and said counter electrode; and
    an alkaline electrolyte present in an amount sufficient to provide reactions in said gas generating electrode and in said counter electrode; and
    means for electrically connecting said gas generating electrode and said counter electrode, and means for supplying a current flow between said gas generating electrode and said counter electrode for generating a predetermined quantity of gas by said gas generating electrode, for release from said opening of said galvanic cell.

2. An actuating apparatus for means for dispensing solids and fluids, or transporting mediums, including the device defined in claim 1, which also possesses means connecting said opening of said galvanic cell and said dispensing means or said transporting medium, for supplying gas to said actuating apparatus for operating said dispensing means or said transporting medium.

3. The device defined in claim 2 wherein an electrical circuit and adjustable resistance is provided to control gas generation.

4. The device defined in claim 2 containing means to open the circuit provided by direct current upon reaching a predetermined gas pressure and to close said circuit when said gas pressure falls below a predetermined value.

5. The device defined in claim 2 that releases the generated gas in pulses.

6. The actuating apparatus defined n claim 2 wherein said means includes a barostatically operated device containing a pressure operated switch that opens an electrical circuit contained with said system when a predetermined pressure is reached and closes when the pressure drops below a predetermined value.

7. The actuating apparatus defined in claim 2 wherein said means includes external electrical circuit which connects said device with a container that emits gas pulses from an opening in said container, said container interiorly having a plurality of springs adjacent one another and means in concert with said springs to seal off an opening in said device from the container at the location where said device and container are connected, the emission of a gas pulse from said opening in said container being the result of the completion of the electrical circuit that includes said device.

8. The apparatus having means defined in claim 2 for taking electrochemical measurements in working combination with a nonreactive tube having an opening at one end, and having a hydrogen electrode that is inserted into an open end of said nonreactive tube, the device that generates said hydrogen gas being secured to said tube at the other end thereof.

9. The apparatus including means defined in claim 2 for dispensing fluid in working combination with a container comprising a cylinder having a movable piston located therein, means connecting said piston at one end to a valve located at the opening through the end of said cylinder at the other end of said means, wherein as the said piston in said cylinder moves away from said valve, said connecting means causes said valve to open and releases hydrogen produced by said device into the atmosphere.

10. The apparatus defined in claim 9 wherein the connecting means is attached at one end to an electric switch.

11. The apparatus defined in claim 10 wherein the valve comprises a non porous thread that moves in an opening through a plate fixed at the end of said cylinder adjacent said cell, thus forming a valve to the atmosphere which is closed as long as said non porous thread has not moved through said opening.

12. The apparatus defined n claim 10 wherein said connecting means comprises a plurality of balls attached to a wire forming a chain, said chain being capable of moving through an elastic pipe situated at the end of said cylinder adjacent said cell, the length of said pipe being sufficient to contain two balls of the chain therein to seal off said pipe, said balls forming a valve like action in said pipe, the valve being opened when the last ball of said chain has passed through said pipe.

13. The device defined in claim 1 for generating hydrogen gas in an adjustable quantity wherein said electron-conducting porous body of said gas generating electrode forming a part of said housing includes a hydrophilic, electrolyte-receiving portion and a hydrophobic, gas-receiving portion, and a porous hydrophobic layer adjacent to and in engagement with said porous body, for preventing electrolyte from leaving the galvanic cell;

and wherein said counter electrode includes an oxidizable metal which serves in countercapacity to said gas generating electrode;

and includes means for excluding air from said galvanic cell, and for excluding oxygen from the pores of the gas generating electrode.

14. The device defined in claim 13 wherein said oxidizable metal is selected from the group consisting of zinc, calcium, lead and copper.

15. The device defined in claim 14 wherein said oxidizable metal is zinc powder or zinc gel and said cell operates at a voltage of about 0.4 V or less.

16. The device defined in claim 15 wherein said zinc cell is short circuited via low resistance and contains sealing means to prevent entrance of air into said cell when said cell starts generating gas to actuate said means for dispensing or transporting.

17. The device defined in claim 15 wherein said oxidizable metal is zinc gel containing said electrolyte is situated within said housing.

18. The device of claim 13 wherein said porous body of said gas generating electrode comprises a metal from Group VIII of the Periodic Table of elements selected from the group consisting of platinum, palladium and nickel, alone or in combination with carbon, said metals having low overvoltage with respect to the evolution of the gas at said electrode.

19. The device defined in claim 1 for generating oxygen gas in an adjustable quantity wherein said electron-conducting porous body of said gas generating electrode forming a part of said housing includes a hydrophilic, electrolyte-receiving portion and a hydrophobic, gas-receiving portion, and a porous hydrophobic layer adjacent to and in engagement with said porous body, for preventing electrolyte from leaving the galvanic cell;

and said counter electrode includes a reducible oxide which serves in countercapacity to said gas generating electrode; and means for electrically connecting said gas generating electrode and said counter electrode, and for establishing a current flow between said gas generating electrode and said counter electrode for generating a predetermined quantity of gas by said gas generating electrode, for release from said opening of said galvanic cell.

20. The device defined in claim 19 wherein said reducible oxide is selected from the group consisting of manganese dioxide, silver oxide, mercury oxide and nickel oxide.

21. The device defined in claim 20 wherein the said reducible oxide is in the form of a porous tablet of a manganese dioxide and is situated within said housing.

22. The device defined in claim 19 wherein said reducible oxide is selected from the group consisting of nitrate is ammonium nitrate.

23. The device defined in claim 22 wherein charcoal powder is blended with said Raney nickel powder.

24. The device defined in claim 22 wherein said gas generating electrode generates oxygen gas and comprises Raney nickel powder in admixture with a hydrophobic resin powder selected from the group consisting of polytetrafluoroethylene and polyethylene.

25. The device defined in claim 1 wherein said gas generating electrode comprises Raney-metals of the Group VIII of the periodic table or noble metals selected from the group consisting of Pt, Pd and platinum containing metals.

26. The device defined in claim 25 wherein said gas generating electrode generates hydrogen gas and comprises a Raney nickel powder bound with a porous foil of polytetrafluoroethylene metal rolled into a net of nickel, said rolled nickel net being a current conductor.

27. The device defined in claim 1 wherein said opening in said housing to releases generated gas resulting from electrochemical activity within said cell and air is excluded from said device by valves which allow a one directional flow of the generated gas to actuate.

28. A plurality of devices as defined in claim 1 connected in series and mounted in a potentiometer ring in working combination with a fluid dispenser comprising a cylindrical container having a dispensing opening at a first end and having within said container fluid material to be dispensed, and a piston, within said cylindrical container and said fluid being positioned between said piston and said dispensing opening said piston being electrically actuated to dispense said fluid through said opening, the resistance of said potentiometer serving to regulate the current thereby determining the dispensing rate of said fluid dispenser.

* * * * *